United States Patent [19]
Feinberg et al.

[11] Patent Number: 5,276,017
[45] Date of Patent: Jan. 4, 1994

[54] THERAPEUTIC AND DIAGNOSTIC APPLICATIONS OF TROPHO-UTERONECTIN (TUN) MANIPULATION

[75] Inventors: Ronald F. Feinberg, Cherry Hill, N.J.; Harvey J. Kliman, Philadelphia, Pa.

[73] Assignee: Trustees of the University of Pennsylvania, Philadelphia, Pa.

[21] Appl. No.: 587,395

[22] Filed: Sep. 25, 1990

Related U.S. Application Data

[63] Continuation-in-part of Ser. No. 583,034, Sep. 14, 1990.

[51] Int. Cl.$^5$ .............................................. A61K 37/00
[52] U.S. Cl. ..................................................... 514/21
[58] Field of Search ...................... 424/422, 423, 430; 435/240.1; 514/21

[56] References Cited

U.S. PATENT DOCUMENTS 4,894,326  1/1990  Matsuura et al. ..................... 435/7

OTHER PUBLICATIONS

Feinberg et al., "Abstract", vol. 12, 1991, p. 387.
Kliman et al., "Purification, characterization and in vitro differentiation of cytotrophoblasts from human term placentae," Endocrinol. 118: 1567–1582 (1986).
Matsuura et al. (J. Biol. Chem. 263, 3314–22 (1988).
Kao et al., Dev Biol. 130:693–702 (1988).
Stroop et al., "Localization of herpes simplex virus in the trigeminal and olfactory systems in the mouse central nervous system during acute and latent infections by in situ hybridization," Lab. Invest. 51:27–38 (1984).
Kalofonos et al., "Antibody guided diagnosis and therapy of brain gliomas using radiolabeled monoclonal antibodies against epidermal growth factor receptor and placental alkaline phosphatase," J Nucl Med 30:1636–45 (1989).
A. Gleicher, N, el RA. (1988) "The reproductive autoimmune failure syndrome," Am J Obstet Gynecol 159:223–7.
Helmer et al. "Intrauterine infusion of highly enriched bovine trophoblast protein-1 complex exerts an antiluteolytic effect to extend corpus luteum life span in cyclic cattle," J Reprod Fertil 87:89–101 (1989).
Jones, R. C. "Blastocyst attachment in the ovariectomized rat treated with an intrauterine injection of luteinizing hormone-releasing hormone (LRH)," Acta Endocrinol (Copenh) 103:266–8 (1983).
Ekman et al., "Intracervical instillation of PGE2-gel in patients with missed abortion or intrauterine fetal death," Arch Gynecol 233:241–5 (1983).
Zhu et al. "The effect of intrauterine devices, the stainless steel ring, the copper T220, and releasing levonorgestrel, on the bleeding profile and the morphological structure of the human endometrium—a comparative study of three IUDs. A morphometric study of 96 cases," Contraception 40:425–38 (1989).
Botelho et al. "cAMP analog antagonists of cAMP action," Methods Emzymol 159: 159–72 (1988).
Botelho et al. in "Inhibition of cAMP-dependent protein kinase by adenosine cyclic 3'-, 5'-phosphorodithioate, a second cAMP antagonist," J Biol Chem 263:5301–5 (1988).
Miyagi et al., "Comparative hemodynamic effects of intravenous dobutamine and dibutyryl cyclic AMP, a new inotropic agent, in severe congestive heart failure," J Cardiovasc Pharmacol 15:138–43 (1990).
Berg et al., "Effects of different phsophodiesterase-inhibiting drugs on human pregnant myometrium: an in vitro study," Arch Int Pharmacodyn Ther 290:288–92 (1987).

(List continued on next page.)

*Primary Examiner*—Douglas W. Robinson
*Assistant Examiner*—Kristin K. Larson
*Attorney, Agent, or Firm*—Woodcock Washburn Kurtz Mackiewicz & Norris

[57] ABSTRACT

Therapeutic and diagnostic applications by the manipulation of a unique protein produced by trophoblasts and defined by the monoclonal antibody FDC-6 are provided by this invention.

2 Claims, 3 Drawing Sheets

OTHER PUBLICATIONS

Tortora et al., "An antisense oligodeoxynucleotide targeted against the type II beta regulatory subunit mRNA of protein kinase inhibits cAMP-induced differentiation in HL-60 leukemia cells without affecting phorbol ester effects," Proc Natl Acad Sci USA 87:705-8 (1990).

Frydman et al., "Phase I clinical trial of monoclonal anti-human chorionic gonadotropin antibody in women with an ectopic pregnancy," Fertil Steril 52:734-8 (1989).

Skarp et al., "Use of a human monoclonal anti-cytomegalovirus antibody for the treatment of severe cytomegalovirus after renal transplantation," Transplant Proc 22:234 (1990).

Ehrlich, et al., "Human and primate monoclonal antibodies for in vivo therapy," Clin. Chem. 34/9:1681-1688 (1988).

Liu et al., "Contraception in mares heteroimmunized with pig zonae pellucidae," J Reprod Fertil 85:19-29 (1989).

A. Gonzalez, et al., "Immunological approaches to contraception in dogs," J. Reprod. Fert., Suppl. 39: 189-198 (1989).

Feinman et al., "8-Bromo-3'5' stimulates the endocrine activity of human cytotrophoblasts in culture," J. Clin end Metab 63:1211-1217 (1986).

Matsuura et al., "The oncofetal domain of fibronectin defined by monoclonal antibody FDC-6: its presence in fibronectins from fetal and tumor tissues and its absence in those from normal adult tissues and plasma," Proc Natl Acad Sci USA 82:6517-21 (1985).

I. Kharat, et al., "Analysis of menstrual records of women immunized with anti-hCG vaccines inducing antibodies partially cross-reactive with hLH," Contraception, vol. 41, No. 3:293-299 (1990).

E. Engvall, et al., "Binding of soluble form of fibroblast surface protein, fibronectin, to collagen," Int. J. Cancer, 20:1-5 (1977).

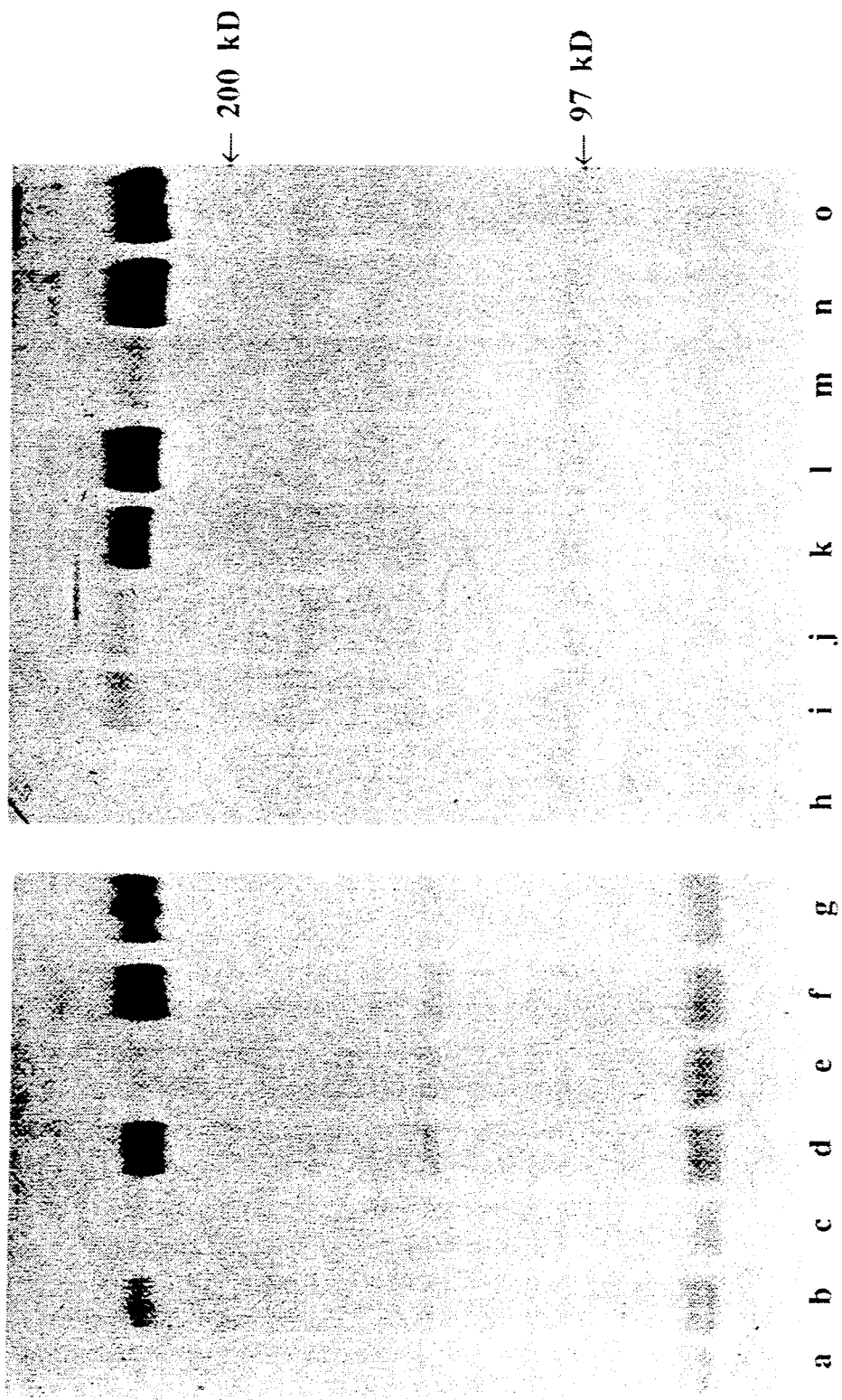

FIG. 3a
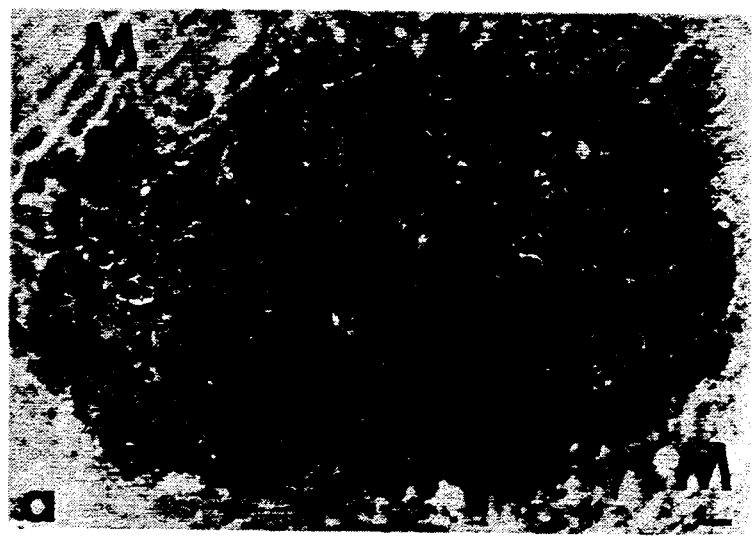
FIG. 3b

THERAPEUTIC AND DIAGNOSTIC APPLICATIONS OF TROPHO-UTERONECTIN (TUN) MANIPULATION

CROSS REFERENCE TO RELATED APPLICATIONS

This application is a continuation-in-part of co-pending application U.S. Ser. No. 07/583,034 filed Sep. 14, 1990.

FIELD OF THE INVENTION

The present invention relates to the field of mammalian reproduction and in particular, the invention relates to therapeutic and diagnostic applications through the manipulation of the protein, tropho-uteronectin. More particularly, therapeutic and diagnostic applications relating to fertility enhancement, contraception and contragestion are provided.

BACKGROUND OF THE INVENTION

In the field of mammalian reproduction, many diagnostic procedures exist to aid the reproduction practitioner in making a diagnosis and choosing an appropriate course of action.

Currently, infertility in humans is defined as one year of unprotected coitus without conception. Approximately 10-15% of couples are affected by infertility. The risk of infertility is doubled for women between the ages of 35 to 44 as compared to women between the ages of 30 and 34. Approximately 600,000 couples sought professional help during the year 1968. However, in the early 1980's this number increased to over 2 million visits per year for infertility. Changes in fertility patterns will have a significant impact on the make-up of populations. It has been calculated that by the middle of the next century, the population in the United States will decline without immigration. Furthermore, the percent of people over the age of 65 will increase to over 23% in the next 100 years, resulting in an older and smaller work force.

In the United States, the majority of infertility can be accounted for by problems in the female. Evaluating a female for infertility can be complex. Examination of the fallopian tubes is an important early step in mammalian fertility evaluation due to the increased evidence of pelvic inflammatory disease. Currently, a hysterosalpingogram (HSG) is the procedure of choice to examine the patency of the fallopian tubes. In addition to HSG, hysteroscopy which is the direct examination of the uterus by a fiber optic device, is important to determine the presence of endometrial polyps, submucous leiomyomas, and other abnormalities within the uterus itself.

Another category of diagnostic procedures includes examination of ovarian function including ovulation and the secretion of progesterone during the luteal phase of the menstrual cycle. Ovarian function can be crudely assessed by measuring basal body temperatures during the menstrual cycle and cervical mucous testing around the time of ovulation. More accurate testing can be performed by measuring luteinizing hormone, a pituitary hormone which induces ovulation after a mid-cycle surge. Finally, serum progesterone levels can be measured to assess for normal luteal phase of the menstrual cycle.

The endometrium itself can be directly assessed by performing an endometrial biopsy three days before the suspected onset of menses. In assessing a mammalian endometrium, current gynecology and infertility physicians depend on pathologists to examine endometrial biopsies by hematoxylin and eosin staining of paraffin embedded specimens. For infertility patients, the reading of these biopsies provides information about the day of the cycle following ovulation, the adequacy of the luteal phase, and other potential data, such as infection, inflammation, or neoplasia of the endometrium. However, in most cases there is no evaluation of the functional and biochemical quality of the endometrium, and often no histologic reading to explain a patient's infertility problem.

Finally, the infertility patient could undergo endoscopic examination through an incision in the abdomen to directly visualize the external surfaces of the ovary, fallopian tubes and uterus to visualize any gross pathology which was not detected by previous examinations.

A high percentage of women who are unable to carry a pregnancy to full term undergo spontaneous abortion generally within the first six weeks. Pregnancy loss during the first six weeks has been shown to be as high as between 15 and 20%. Furthermore, the chance of a successful live birth after consecutive abortions without a live birth is only 40-50%.

Localization of trophoblast tissue, e.g., ectopic pregnancies and metastatic gestational trophoblastic disease are particularly challenging. The manifestations of tubal pregnancy are multiple. Amenorrhea, vaginal spotting or bleeding, abdominal or pelvic pain, presence of a pelvic mass and an increased body temperature may be present in a variety of combinations in the presence of ectopic pregnancy. Laboratory testing for suspected ectopic pregnancy includes hemoglobin and hematocrit, white blood cell count, urine and serum $\beta$-HCG pregnancy test, ultrasound including vaginal probe ultrasound, culdocentesis (a diagnostic procedure to detect blood in the peritoneum), curettage of the endometrium to rule out the presence of products of conception within the uterus, laparoscopy and finally in emergency cases, laparotomy. Given the wide variability of patient presentation and the course of ectopic pregnancy, the accurate diagnosis of this disorder is the most difficult one to make in obstetrics and gynecology. In one study of three hundred women, approximately a third were seen more than once, and 11% were seen more than twice before the correct diagnosis was made. In addition, in a recent study of deaths from ectopic pregnancy, more than half of the cases were misdiagnosed leading to fatal maternal outcome. Clearly, accurate and rapid diagnosis and treatment of an ectopic pregnancy would be an important advance for the field of obstetrics and gynecology.

The current modalities for detecting metastatic gestational trophoblastic disease include serum hCG level determination, chest x-ray, pelvic ultrasound, CT scan of the abdomen pelvis and head. Like in other solid tumors, small metastases can be missed by these procedures. The knowledge of the presence of metastases is critical for the successful treatment of this and other tumors. Therefore, a method which can localize and detect small quantities of trophoblast would be very helpful for the treatment of this disease.

A teratogen is any agent which induces alteration in form or function of a fetus when administered during pregnancy. In considering the effects of drugs during pregnancy, gestation is generally divided into three periods: (1) the ovum and fertilization to implantation; (2) the embryonic period from the second to the eighth week; and (3) the fetal period, from after eight completed weeks until term.

Given the wide variety of drugs available as well as many complex factors during gestation, it has been concluded by many people in the field of mammalian reproduction that there is a severe lack of information regarding the majority of drugs, and the potential detrimental effects of these drugs during pregnancy. The Food and Drug Administration in 1979 established five categories for medications with regard to possible adverse fetal effects. Category A includes drugs which in controlled studies in humans have demonstrated no fetal risk. There are very few drugs in this category and they include multi-vitamins and pre-natal vitamins. Category B are drugs in which animal or human studies have not demonstrated a significant risk. These drugs have been shown to have no animal fetal risk but no evidence is available in humans. Penicillins fall into this category. Category C are drugs in which no adequate studies in either animals or humans have been performed. Many drugs taken during pregnancy fall into this category. Category D are drugs in which there is evidence of fetal risk but certain clinical benefits outweigh the risks. An example are the anti-convulsants. Category X are drugs with proven fetal risk which are not outweighed by any benefits.

Contragestion, or post-coital contraception is currently practiced by two basic methods: surgical and medical. In the 1970's the "morning after pill" (diethylstilbestrol) was popular as a post-coital contraceptive method. More recently, the use of the anti-progesterone RU-486 has gained wide acceptance in Europe to terminate pregnancy soon after fertilization and implantation. During the first trimester, the most common technique to end a pregnancy is by surgical abortion. Surgical abortions generally involve cervical dilation and curettage or vacuum aspiration. Finally, after the first trimester, labor inducing medications such as oxytocin and prostaglandins can be utilized to induce premature delivery and thus the termination of pregnancy. The medical techniques described above are known to have a number of adverse reactions and potential complications. The surgical technique can lead to uterine rupture, hemorrhage, and infection.

In the United States, the commonly employed contraceptive techniques include oral steroidal contraceptives, injected or implanted steroidal contraceptives, intra-uterine devices, physical, chemical, or physicochemical barrier techniques, withdrawal, sexual abstinence around the time of ovulation, breast feeding, and permanent sterilization. In addition to the high failure rates of some of these methods, a number of these methods have serious potential complications for the users. For example, in addition to metabolic changes induced by oral contraceptives, there is possibly an increased risk of neoplasia, nutritional disorders, cardiovascular effects, thromboembolism and even death.

In vitro fertilization (IVF) requires the removal of ova from a mammalian ovary, and exposure of these ova to sperm outside the body. Fertilization of each ovum requires that at least one living sperm penetrates the zona pellucida (outer covering) of the ovum and fuses with the pronucleus. Once this has occurred and the ova are fertilized, they can be transferred to a uterus where they can become implanted on the uterine wall. If implantation occurs, the pregnancy can proceed as if fertilization had occurred within the body. In vitro fertilization has gained widespread professional and public acceptance. However, despite the ever increasing frequency and refinement of this procedure, in vitro fertilization attempts most often do not result in pregnancy. In vitro pregnancy rates are currently only about 15 to 20 percent. For a variety of reasons, exposing the ova to sperm does not necessarily result in fertilization. Furthermore, even where the ova is fertilized, the placement of the ova in a uterus usually does not result in normal implantation. The low success rate of IVF often leads to an excessive financial and psychological burden for the infertile couple.

Other assisted reproductive technologies include two modifications of the IVF technique. The first is gamete intra-fallopian transfer (GIFT), the second is zygote intra-fallopian transfer (ZIFT). In the GIFT procedure, the retrieved oocyte and sperm are mixed together and placed back into the fallopian tube where fertilization takes place. The fertilized zygote then travels down through the fallopian tube into the endometrial cavity, where implantation may or may not take place. The ZIFT procedure allows for fertilization to take place in vitro as in standard IVF, and then the fertilized zygote is placed back in the fallopian tube where it then travels down into the uterus to implant. Finally, it is becoming realized that the hyper-stimulation protocols necessary to retrieve many oocytes from the donor woman may have deleterious effects on the endometrium itself and decrease the rates of implantation. Two basic procedures have been utilized to help overcome this problem. The first is considered non-stimulated oocyte retrieval. A single egg is retrieved, allowed to be fertilized and placed back into the fallopian tube or uterus for implantation. The other technique involves the hyper-stimulation portion of the IVF procedure to retrieve the eggs and allow for fertilization in vitro. The zygotes are then frozen to be placed back into the patient after several normal cycles, with the hope that the endometrium will be more receptive to implantation. All of these techniques attempt to maximize the quality of the eggs, zygotes produced after fertilization and the receptivity of the endometrium. Any procedure which would enhance the implantation rate above the standard 15 to 20% would have a marked positive effect on any of these technologies.

Notwithstanding the work reported in this field, a need still exists for improved diagnostic and therapeutic applications in the field of mammalian reproduction.

SUMMARY OF INVENTION

This invention provides a novel method of locating trophoblastic tissue, such as an ectopic pregnancy, in a mammal. The method comprises administering to a mammal a radiolabeled TUN antibody, e.g., $^{125}I$ labeled FDC-6, in an amount sufficient to bind to said trophoblastic tissue and detect the label bound to said TUN antibody, whereby the location of said trophoblastic tissue is determined. In a preferred embodiment, the labeled antibody is coupled to a means for treating the located trophoblastic tissue, such as the pharmacologic toxin, methotrexate. Applicants have recognized the role of trophoblasts as a producer of the protein TUN. Thus, the method of this invention permits non-invasive diagnosis and treatment of pathological conditions involving trophoblastic tissue, such as ectopic pregnancies and metastatic gestational trophoblastic disease.

The invention further provides a novel infertility screening test comprising assaying at least one bodily fluid or cell type from a mammal suspected of being infertile for the presence of TUN autoantibodies. Applicants have recognized the association of the protein TUN with normal mammalian reproduction. Thus, the method of this invention provides a tool for diagnosing mammals with an autoimmune infertility.

This invention further provides a novel method of screening pharmacologic agents suspected of adversely interfering with fertilization, implantation, attachment or gestation of a conceptus, comprising the steps of culturing mammalian trophoblasts, contacting the trophoblasts with at least one of said agents and assaying the trophoblasts for at least one trophoblast-produced compound to determine the relative effect on the nature or production of said trophoblast-produced compound resulting from said contact with said one of said agents. Applicants have recognized that trophoblast-uterine extracellular matrix interactions are critical to mammalian implantation of a conceptus and that a variety of compounds, such as TUN, are produced by cultured mammalian trophoblasts. Thus, the method of this invention provides information as to the impact of a pharmacologic agent on a major cell type critical to mammalian reproduction and maintaining fetal well-being.

This invention further provides a novel method for increasing the probability that a conceptus will become implanted in a mammalian uterus. The method comprises infusing TUN into the uterine cavity at about the time the uterus will be contacted with the conceptus, said infusing introducing a sufficient amount of TUN onto the surface of the uterine cavity to increase the probability that implantation will occur. Alternatively, the method comprises contacting an ovum or conceptus with a sufficient amount of TUN prior to introduction of said ova or conceptus into a female mammalian reproductive tract, to increase the success rate of assisted reproductive technologies. Applicants have recognized that during normal mammalian pregnancy, TUN has been localized in at least several locations including the implantation zone where trophoblastic cells make contact and attach to the uterus and within the chorionic membrane where trophoblastic cells make direct contact with the maternal decidua. Thus the method of this invention changes the local environment of the surface of the endometrium at about the time the uterus will be contacted with the conceptus thereby increasing the chance that a conceptus will become implanted in the uterus.

The invention further provides a novel method of augmenting TUN synthesis in a mammal comprising administering to the mammal an agent which stimulates mammalian trophoblasts in culture to make TUN, such as a cAMP inhibitor or a compound found in the plasma, ECM or maternal decidua of a mammal, in an amount effective to augment TUN synthesis in the mammal. Applicants have recognized that cAMP is potent inhibitor of TUN synthesis in cultured mammalian trophoblasts and that compounds which inhibit the action of cAMP have a stimulatory effect on TUN synthesis. Applicants have further recognized that during normal mammalian pregnancy, TUN has been localized at the implantation zone where trophoblastic cells make direct contact with the maternal decidua. Thus, the method of this invention provides a method to increase the level of TUN synthesis in a mammal.

Further provided by this invention is a novel method of inhibiting TUN synthesis in a mammal. The method comprises administering to said mammal a compound which inhibits TUN synthesis by mammalian trophoblasts in culture, such as cAMP agonists, phosphodiesterase inhibitors and antisense deoxyribooligonucleotide inhibitors, in an amount effective to inhibit TUN synthesis in said mammal. Applicants have recognized the importance of the protein TUN in critical phases of mammalian reproduction, thus inhibiting the production of TUN by the method of this invention, provides inter alia methods of contraception and contragestion.

Further provided by this invention is a novel method of decreasing free TUN in a mammal comprising administering to said mammal TUN antibodies sufficient to bind to at least some TUN in said mammal. Applicants have recognized the importance of the protein TUN in critical phases of mammalian reproduction. Thus, by the method of this invention, anti-TUN antibodies bind to TUN expressed by the mammal and effectively decrease the amount of available or free TUN rendering a pregnancy unable to sustain itself or conception unlikely.

Further provided by this invention is a novel method of sterilizing a mammal. By the method of this invention, a mammal is sterilized by administering to the mammal a TUN antigen in an amount sufficient to raise antibodies to TUN, whereby the probability that a conceptus will become implanted in the uterus is decreased. Applicants have recognized that TUN appears in trophoblasts during mammalian pregnancy. Thus this invention provides a method of raising antibodies against TUN, which would bind to TUN expressed by the mammal thus inducing sterilization or preventing complete attachment of a conceptus to the uterus thus terminating any potential or ongoing pregnancy.

Further provided by this invention is a novel method of producing TUN comprising the steps of culturing mammalian trophoblasts for a time sufficient to produce at least some TUN and separating the TUN thus produced. Applicants have recognized that cultured mammalian trophoblasts produce and secrete intact TUN. Thus, the invention provides a source of TUN for, inter alia, the preparation of antisera, monoclonal antibodies specific to TUN and methods of treatment utilizing TUN.

Applicants have recognized the importance of TUN in critical phases of mammalian reproduction. Accordingly, objects of this invention are to enhance fertility, provide methods of contraception and contragestion and to provide methods of diagnosis by the manipulation of the protein TUN.

BRIEF DESCRIPTION OF THE DRAWINGS

FIGS. 2(a) and 2(b) are photographs of a gel depicting the results of experiments in Example 2, infra.

FIGS. 3(a) and 3(b) are photographs of a fixed section depicting the results of experiments in Example 4, infra.

DETAILED DESCRIPTION OF THE INVENTION

Figure 1B:
FIGS. 1(a), 1(b), 1(c) and 1(d) are photographs of a fixed section depicting the results of experiments in Example 1, infra.

"Tropho-Uteronectin" (TUN) as used herein refers to a class of proteins which bind to FDC-6 and are produced by mammalian trophoblasts. The immunological binding partner (FDC-6), although previously thought not to bind to normal human adult tissues, binds to the previously unknown protein (TUN) produced by certain normal adult tissues at critical times and locations of reproduction.

"FDC-6" as used herein refers to the monoclonal antibody defining the oncofetal structure of fibronectin as disclosed in U.S. Pat. No. 4,894,326. U.S. Pat. No. 4,894,326 is incorporated by reference as if fully set forth herein.

U.S. Pat. No. 4,894,326 discloses an IgGI monoclonal antibody (FDC-6) which defines a fibronectin structure or structures located between the "Hep-2" and the "Fib-2" domains in the COOH-terminal region of fibronectins isolated from hepatoma, sarcoma, and fetal fibroblasts. It is disclosed that this antibody discriminates between two general classes of human fibronectin. First, fibronectin from fetal connective tissue, placenta, amniotic fluid, hepatoma, and colon carcinoma as well as cell lines from fetal tissue, hepatomas, and sarcomas, was characterized by the presence of the FDC-6 defined structure and by a high molecular weight. Second, fibronectin from normal adult tissues and plasma was characterized by a lower molecular weight and lack of reactivity with FDC-6, and is therefore devoid of the FDC-6 defined structure. The FDC-6 defined structure is referred to as the "oncofetal structure," and fibronectin containing this structure has been called "oncofetal fibronectin." Fibronectin from normal adult tissues and plasma lacking the oncofetal structure, is characterized as "normal fibronectin." Development of fibronectin from fetal to adult form is disclosed to be associated with loss of the oncofetal structure defined by the FDC-6 antibody, and oncogenic transformation is disclosed to be associated with activation in synthesis of the oncofetal structure defined by the FDC-6 antibody. Since the structure defined by FDC-6 antibody expressed in oncofetal fibronectin is a useful marker of cancer, it is disclosed that the FDC-6 antibody and other antibodies raised against the oncofetal fibronectin structure will be useful for diagnosing human cancer and for monitoring and implementing various cancer treatments.

The monoclonal antibody FDC-6, a product of hybridoma cell line ATCC No. HB9018, is suitable for use in this invention, as a specific probe for a variety of immunoassays such as, immunohistochemical localization and immunoblot analyses. FDC-6 can be prepared substantially as described in U.S. Pat. No. 4,894,326. Briefly, the murine monoclonal antibody FDC-6 was established following immunization with fibronectin isolated from human hepatoma cells. The hybridoma ATCC No. HB9018 can be selected by positive reactivity of its antibody (FDC-6) with fibronectins from hepatoma, fibrosarcoma, and fetal fibroblasts and by negative reactivity with fibronectin from plasma.

Other more specific TUN antibodies are expected to be useful in this invention and are described in detail below.

Method of Producing TUN

TUN is produced by the method of this invention by culturing mammalian trophoblasts for a time sufficient to produce at least some TUN and separating the TUN thus produced.

"Culturing Mammalian Trophoblasts" as used herein refers to the following procedure: Initially, mammalian trophoblasts from placenta are isolated by the method of Kliman et al., "Purification, characterization and in vitro differentiation of cytotrophoblasts from human term placentae," *Endocrinol.* 118:1567-1582 (1986). The isolated trophoblasts are typically cultured in a low percent of serum (generally less than 10% fetal calf serum) with or without precoating of the culture surface with an extracellular matrix component, such as laminin or type I collagen. This is to minimize the quantity of extraneous, nontrophoblast proteins in the media, yet permit normal trophoblast attachment, spreading, and syncytialization. Subsequently, when active TUN synthesis is initiated, generally after approximately 24-48 hours, the media is switched to serum-free conditions. Trophoblasts continue to actively produce TUN when cultured in serum free media. A concentration of 0.1-1.0 mg/dl of TUN in the media 24 hours after changing to serum-free conditions can generally be expected.

Human choriocarcinoma cell lines, e.g., JEG-3 cells are expected to be useful in producing TUN. These cells could be used to generate media containing TUN. In another alternative, cosmids containing the TUN gene, or active fragments of TUN gene, could be created and introduced into cells to generate specific protein fragments of TUN.

Once such media is obtained, TUN is readily separated by a variety of techniques. For example, TUN can be specifically bound to and eluted from an affinity column, e.g., "Sepharose", as described in the method of Engvall and Ruoslahti (*Int. J. Cancer* 20, 1-5 (1977)) or an affinity column of FDC-6 or any other TUN antibody bound to the gel can be used to bind and subsequently elute TUN, as described in the method by Matsuura et al. (*J. Biol. Chem.* 263, 3314-22 (1988)). Additionally TUN can be separated and transferred to nitrocellulose following polyacrylamide gel electrophoresis by known techniques.

Once TUN is separated, it can be treated with various proteases, such as thermolysin, trypsin, cathepsin D, and Achromobacter Protease I, or other enzymes known to specifically digest fibronectins into discrete glycopeptide fragments. The fragments of interest, once purified by affinity chromatography or gel electrophoresis, can be assayed in several ways. For example, the TUN fragments can be tested in a trophoblast attachment assay (Kao et al., *Dev Biol,* 130:693-702 (1988)), to determine if the fragments contain regions which promote stable trophoblast attachment, spreading, and syncytialization, either on plastic, glass, or any other ECM substrate. The TUN fragments can then be added to serum-free media or used in a pre-coating medium. Freshly isolated trophoblasts, which do not normally spread and syncytialize in serum-free conditions, bind to active TUN fragments and behave similarly to cells in serum-containing conditions. Additionally, the TUN fragments can be assayed for the presence of the oncofetal domain, or any other domain, via immunoblots or enzyme-linked immunoassays with anti-fibronectin antibodies by known techniques.

TUN thus produced can be injected into mice or other animals for the generation of an antibody response and the preparation of many different monoclonal antibodies to TUN by known techniques. See e.g., "Antibodies, A Laboratory Manual," Cold Spring Harbor (1988), which manual is incorporated by reference as if fully set forth herein.

As another example, antibodies can be generated to fragments active in the trophoblast attachment assay. These antibodies can serve as inhibitors of trophoblast attachment and the implantation process itself. These antibodies would be expected to be more potent than FDC-6 antibodies as they bind to active regions of TUN.

Once anti-TUN antibodies are generated, as described above, those antibodies which specifically bind to TUN, but not other fibronectins can be identified. An assay expected to be useful in identifying these antibodies is based on a comparative immunoassay utilizing TUN and other fibronectins, such as amniotic fluid or human plasma fibronectins. For example, if a particular anti-TUN antibody, prepared as described above, binds to TUN but not other fibronectins, it would be deemed specific for TUN.

Anti-TUN antibodies are expected to bind to specific regions unique to TUN to alter its activity, such as its binding capability to cells or extracellular matrix.

Diagnosis

The term "Conceptus" as used herein refers to the sum of derivatives of a fertilized ovum at any stage of development from fertilization to birth, including extra-embryonic membranes as well as the embryo or fetus.

Further provided by this invention is a method to localize trophoblastic tissue in a mammal. By the method of this invention, a mammal is administered an effective amount of a radiolabeled TUN antibody and the radiolabeled antibody coupled to TUN in the trophoblastic tissue is detected.

Detection is conveniently accomplished by nuclear scan.

Conveniently, FDC-6 is a suitable antibody for use in this invention. Other TUN antibodies prepared as described above are also expected to be suitable for use in the invention.

Conveniently, $^{125}$I or technetium-99 are expected to be suitable radiolabels.

Examples of trophoblastic tissue to be localized include ectopic pregnancies and metastatic gestational trophoblastic disease.

Radiolabeling of the antibody and detection can be performed substantially as described in Goldenberg DM. (1990) "Cancer imaging with radiolabeled antibodies," *Front Radiat Ther Oncol* 24:90-5 (1990) and Kalofonos et al. "Antibody guided diagnosis and therapy of brain gliomas using radiolabeled monoclonal antibodies against epidermal growth factor receptor and placental alkaline phosphatase," *J Nucl Med* 30:1636-45 (1989), which papers are incorporated by reference as if fully set forth herein.

In a preferred embodiment, the labeled antibody can be coupled to a means for treating the localized trophoblastic tissue. For example, $^{125}$I labeled or methotrexate-bound anti-TUN antibodies could be administered to a mammal.

In another aspect of this invention, an infertility screening test is provided. At least one bodily fluid or cell type from a mammal suspected of being infertile is assayed for the presence of TUN autoantibodies.

Conveniently, the presence of autoantibodies that bind to TUN can be assayed by basic enzyme-linked immunoassay (ELISA) (where purified TUN is immobilized on a plastic surface, and the subject's bodily fluid, e.g., serum or cervicouterine secretion, is applied to these wells in various dilutions), or immunoblot techniques. A positive test would occur by using a marker secondary anti-human antibody, which would only bind in the assay if the patient's bodily fluids contained an anti-TUN autoantibody.

Bodily fluids expected to be useful include, e.g., plasma, serum and cervicouterine aspirates. Examples of cell types expected to be useful include an endometrial biopsy. Generally, any bodily fluid or cell type associated with TUN in a fertile control are believed to be useful.

Certain causes of previously unexplained infertility are believed due to an autoimmune process leading to endogenous production of anti-TUN antibodies. In one aspect, this autoimmune process is believed to prevent the proper biological function of TUN, thus preventing implantation initially or leading to repetitive miscarriage later in pregnancy.

There is clear precedence for autoimmune infertility. It has been shown that patients who have general autoimmune diseases have a high incidence of reproductive failure. A. Gleicher N, el RA. (1988) "The reproductive autoimmune failure syndrome," *Am J Obstet Gynecol* 159:223-7.

The first step in treating mammals with autoimmune infertility is a screening method to identify this group. Once identified, these patients might benefit from specific treatments used for patients with autoimmune diseases, such as immunosuppressive therapy.

In another aspect of this invention, a method of screening pharmacologic agents suspected of adversely interfering with fertilization, implantation, attachment or gestation of a conceptus, comprising the steps of culturing mammalian trophoblasts, contacting the trophoblasts with at least one of said agents and assaying the trophoblasts for at least one trophoblast-produced compound to determine the relative effect on the nature or production of said trophoblast-produced compound resulting from said contact with said one of said agents.

Trophoblasts can be cultured as described previously. After contact with the agent, the trophoblasts are generally continued in culture for a time sufficient to produce at least one trophoblast-produced compound. The agent can be added to the culture at about the agents typical biologically active plasma concentrations. Active metabolites of pharmacologic agents can also be tested in this assay.

Suitable trophoblast-produced compounds to be assayed for include e.g., TUN, human chorionic gonadotropin (hCG), human placental lactogen (hPL) and progesterone.

Assays for the trophoblast-produced compound TUN are as described previously. Assays for other known trophoblast-produced compounds such as hCG and progesterone are known.

Any pharmacologic agent which has the potential to modulate any trophoblast-produced compound, and in particular diminish TUN synthesis, should not be administered to pregnant mammals. If e.g., a particular medication inhibited TUN production by trophoblasts at a pharmacologic concentration known for that mammal in the media, the medication would be described as an active inhibitor of TUN in the trophoblast toxicity assay. It might, consequently, be judged by the Food and Drug Administration as potentially harmful to human pregnancy.

Fertility Enhancement

In another aspect of this invention, a method of increasing the probability that a conceptus will become implanted in a mammalian uterus is provided. By the method of this invention, TUN is infused into the uterine cavity at about the time the uterus will be contacted with a conceptus, said infusing introducing a sufficient amount of TUN onto the surface of the uterine cavity to increase the probability that implantation will occur.

The time a uterus will be contacted with a conceptus can be e.g., at about the time of presumed implantation during a natural cycle of conception, or the time of assisted reproductive technologies. During assisted reproductive technology, TUN could be applied to the uterine cavity either prior to, during, or after the introduction of the fertilized or unfertilized ovum to the uterus or fallopian tube.

Alternatively, the method comprises contacting an ovum or conceptus with a sufficient amount of TUN prior to introduction of said ovum or conceptus into a female mammalian reproductive tract, to increase the success rate of assisted reproductive technologies.

TUN could be utilized in a variety of ways as are other agents for introduction into the uterus. For example, TUN could be in a dissolved form, either in solution, within a gel, or in a slow release intrauterine device to allow for an appropriate time-dependent concentration in the uterine cavity.

A sufficient amount of TUN is that amount of TUN which when introduced onto the surface of the uterine cavity or contacted with an ova, increases the probability that implantation of a conceptus will occur or increases the success rate of assisted reproductive technologies. Concentrations of TUN in the range from about 0.1 µg/ml to about 1 mg/ml are expected to be useful, since TUN concentrations in human reproductive fluids fall in this range.

It is believed that TUN is the "glue" which facilitates implantation and subsequent attachment of the placenta and membranes to the uterus. Therefore, methods to enhance these processes by therapeutic infusion of TUN into the uterine cavity are provided by this invention. The method changes the local environment of the surface of the endometrium sufficiently to improve the chance of conceptus implantation.

Literature is known describing intrauterine infusions, gels or sponges for the treatment of a variety of conditions. It has been shown that the endocrine function of an ovary could be markedly changed by an intrauterine infusion. Helmer et al. "Intrauterine infusion of highly enriched bovine trophoblast protein-1 complex exerts an antiluteolytic effect to extend corpus luteum life span in cyclic cattle," *J Reprod Fertil* 87:89–101 (1989). It has been shown that rat uteri which received an intrauterine injection of luteinizing releasing hormone had a significantly increased rate of implantation compared to uteri which had no injection. Jones, R. C. "Blastocyst attachment in the ovariectomized rat treated with an intrauterine injection of luteinizing hormone-releasing hormone (LRH)," *Acta Endocrinol* (Copenh) 103:266–8 (1983). In addition to the use of solutions, there are references citing use of gels which are instilled intracervically to facilitate labor and delivery. See e.g., Ekman et al., "Intracervical instillation of PGE2-gel in patients with missed abortion or intrauterine fetal death," *Arch Gynecol* 233:241–5 (1983). Finally, an intrauterine vehicle either similar to those currently existing on the market or modified to facilitate slower release of a pharmacologic agent which might either enhance or decrease the synthesis of TUN could be utilized. An example of such a slow release intrauterine vehicle can be found in Zhu et al. "The effect of intrauterine devices, the stainless steel ring, the copper T220, and releasing levonorgestrel, on the bleeding profile and the morphological structure of the human endometrium—a comparative study of three IUDs. A morphometric study of 96 cases," *Contraception* 40:425–38 (1989).

In another aspect of this invention, a method to augment the level of TUN synthesis in a mammal is provided. This method comprises administering to the mammal an agent which stimulates mammalian trophoblasts cells in culture to make TUN in an amount effective to augment TUN synthesis in the mammal.

Compounds which inhibit the action of cAMP are believed to have a stimulatory effect on TUN synthesis and thus useful in augmenting TUN synthesis as cAMP is a potent inhibitor of TUN synthesis in cultured mammalian trophoblasts.

Pharmacologic agents that are cAMP antagonists can be administered by well known methods such as locally in the intrauterine space, or systemically. This pharmacologic manipulation preferably utilizing a medication with a localized effect to the conceptus and little or no effect systemically.

An effective amount of a cAMP inhibitor is that amount which augments TUN synthesis in the mammal.

Many agents which have been shown to inhibit cAMP action have been identified. See e.g., Botelho et al. "cAMP analog antagonists of cAMP action," *Methods Enzymol* 159: 159–72 (1988). One of the most promising, adenosine cyclic 3'-5'-phosphorodithioate, is described in significant detail by Botelho et al. in "Inhibition of cAMP-dependent protein kinase by adenosine cyclic 3'-, 5'-phosphorodithioate, a second cAMP antagonist," *J Biol Chem* 263:5301–5 (1988).

Other compounds found in the plasma, ECM, or maternal decidua of a mammal are expected to be useful for enhancing TUN synthesis as mammalian trophoblasts have been stimulated in culture, within two days, to synthesize TUN de novo. In addition, trophoblasts which make contact with extracellular matrix (ECM) components are specifically stimulated to make TUN. Therefore, those compounds in plasma, ECM extracts, or maternal decidua which induce TUN synthesis can be readily identified in the in vitro trophoblast culture assay described herein and employed in the method of this invention in an amount sufficient to augment TUN synthesis in a mammal. Such compounds are expected to include steroids, peptides, and glycopeptide hormones, gonadotropins, growth factors, cytokines, antibodies, as well as portions of ECM proteins including other fibronectins, laminin, collagen, entactin, vitronectin, or proteoglycans.

TUN synthesis can be augmented in a mammal about the time the uterus of the mammal will be contacted with a conceptus whereby the chances of the conceptus becoming implanted in the uterus are enhanced.

Thus, methods of increasing the probability that a conceptus will become implanted in a uterus, preferably by infusion of TUN or a compound that augments TUN synthesis in a mammalian uterus, are provided by this invention.

Contraception and Contragestion

In another aspect of this invention, a method of inhibiting TUN synthesis in a mammal is provided comprising administering to said mammal a compound which inhibits TUN synthesis by mammalian trophoblasts in culture in an amount effective to inhibit TUN synthesis in said mammal.

Compounds which inhibit TUN synthesis by mammalian trophoblasts in culture can be selected from the group consisting of cAMP agonists, phosphodiesterase inhibitors and antisense oligonucleotide inhibitors.

Inhibition of TUN synthesis in a mammal has a variety of utilities. For example, a mammal determined to have a level of TUN in excess of a normal fertile control, may be a candidate for TUN inhibition. TUN inhibition can be employed to a level where a method of contraception is provided. Additionally, TUN inhibition can be utilized to terminate a pregnancy and thus provide a method of contragestion.

Pharmacologic manipulation to increase intracellular cAMP levels e.g., within the conceptus is expected to be useful in inhibiting TUN synthesis. Taking the opposite approach described above for augmenting TUN synthesis, any pharmacologic agents which decrease TUN synthesis or expression can be utilized.

The therapeutic use of the cAMP agonist dibutyryl cAMP has been reported. For example, it has been demonstrated that patients with congestive heart failure could be treated with intravenous dibutyryl cAMP. Miyagi et al., "Comparative hemodynamic effects of intravenous dobutamine and dibutyryl cyclic AMP, a new inotropic agent, in severe congestive heart failure," *J Cardiovasc Pharmacol* 15:138–43 (1990). Alternatively, a slow release cAMP agonist might be applied in a suppository form or in a sponge form and placed within the cervix or uterus to effect significant contraceptive or contragestive response by inhibiting the synthesis of conceptus TUN.

Phosphodiesterase inhibiting drugs inhibit the enzyme phosphodiesterase, which breaks down cAMP within the cell. In effect these drugs are believed to increase the intracytoplasmic levels of cAMP in cells within the body. Therefore this class of medications are believed to be useful as inhibitors of TUN synthesis in vivo. Medications such as theophylline, a common phosphodiesterase inhibitor, have been used as a standard treatment for patients with bronchial asthma. In addition, phosphodiesterase inhibitors have been used in pregnant women to relax the smooth muscle of the prematurely contracting uterus. The use of other phosphodiesterase inhibitors such as, Eupaverin, Enprofylline Theophylline, and Papaverine have been described. Berg et al., "Effects of different phosphodiesterase-inhibiting drugs on human pregnant myometrium: an in vitro study," *Arch Int Pharmacodyn Ther* 90:288–92 (1987).

Finally, an alternative approach to decrease mammalian TUN synthesis is antisense oligonucleotide inhibitors. Recently it has been demonstrated that adding oligonucleotide antisense DNA probes to cells causes them to specifically stop producing the corresponding messenger RNA. See e.g., Tortora et al., "An antisense oligodeoxynuoleotide targeted against the type II beta regulatory subunit mRNA of protein kinase inhibits cAMP-induced differentiation in HL-60 leukemia cells without affecting phorbol ester effects," *Proc Natl Acad Sci U S A* 87:705–8 (1990).

An antisense oligonucleotide specific for the oncofetal domain of TUN (e.g., 5'-ATACC-CAGGGTGGGTGAC) can readily be made and be given to a mammal in a variety of ways. For example, the antisense oligonucleotide could be given parenterally via intravenous injection, in slow release form in the subcutaneous tissues, or as a slow release form in a gel or sponge applied to the cervix or intrauterine cavity in an amount sufficient to inhibit TUN secretion. Thus, treatment with an antisense oligonucleotide specific for oncofetal domain-containing fibronectins like TUN, is expected to only prevent the synthesis of TUN, and should not have any untoward systemic effects. The inability of TUN antisense oligonucleotides to inhibit synthesis of other fibronectins could be readily verified in cell cultures which produce non-oncofetal fibronectins.

In contrast to applications used for contraception, contragestion assumes that fertilization has occurred and implantation has begun. Therefore, contragestion is effected by preventing the further development of the conceptus. Thus by inhibiting TUN synthesis, a method of contragestion is provided by preventing the firm and stable attachment of the trophoblasts to the endometrial stroma by inhibiting the synthesis of TUN by the expanding trophoblast shell after implantation has commenced.

Pharmacologic manipulation to yield a method of contragestion can be achieved, as previously described, by introducing cAMP agonists to the local environment of the uterus through a suppository, gel or sponge or by direct systemic treatment with a cAMP agonist such as dibutyryl cAMP; phosphodiesterase inhibitors, which increase cAMP levels by inhibiting the breakdown of the cAMP within the cell, or deoxyoligonucleotide antisense molecules could be applied to the local environment of the uterus through a gel, a suppository, slow release sponge, or directly with a solution vehicle to inhibit the synthesis of TUN. Because of the specificity of this oligonucleotide probe, it may be feasible to administer this agent systemically.

These manipulations are expected to be effective both for intrauterine and ectopic implantations, the majority of which are intratubal implantations. In addition to the potential application of preventing normal pregnancy, pharmacologic manipulation of TUN is expected to be a useful non-surgical, non-invasive alternative to treatment of chromosomally abnormal pregnancies, missed abortions, and incomplete abortions. Termination of tubal ectopic pregnancies could occur by either the direct installation of the pharmacologic agent to the tubal pregnancy via laparoscopic, ultrasonic, or retrograde cervicouterine irrigation.

In another aspect of this invention, a method of decreasing free TUN in a mammal is provided comprising administering to the mammal TUN antibodies sufficient to bind to at least some TUN in the mammal.

In place of the pharmacologic and biochemical manipulation to decrease TUN synthesis described herein, this method applies, either locally or systemically, specific mammalian antibodies against TUN to provide reduction in the levels of free TUN. Unlike the biochemical/pharmacologic manipulations described previously, the use of TUN antibodies relies on the notion that these antibodies directly bind to TUN at a key site (possibly the FDC-6 reactive portion of the oncofetal domain, or other critical sites) which may act as the binding domain to either the ECM, or to the trophoblast or other cells, e.g., uterine cells themselves. This is expected to serve a similar function as decreasing TUN synthesis since the antibodies could compete directly with the binding site within trophoblasts, for TUN. Once this binding is inhibited by the anti-TUN antibodies, a pregnancy would not be able to sustain itself due to lack of adequate blood flow to the developing trophoblastic shell and embryo.

Human anti-TUN monoclonal antibodies, prepared as described supra, are expected to have advantages over the murine monoclonal antibody FDC-6, for example, in that there is a much lower incidence of immune reaction to the humanized form of antibodies. The purified TUN antigen for development of these antibodies is readily prepared by standard biochemical means from cultured trophoblast conditioned media as described herein.

Immunologic interruption of pregnancy has been achieved. For example, it has been shown that when 5 and 25 mg of purified anti-hCG was injected into three patients with ectopic pregnancies, one of these patients completely resolved their tubal pregnancy, while the two others had markedly decreased levels of progesterone and estrogen, suggesting a marked decrease in viability of the pregnancy. Frydman et al., "Phase I clinical trial of monoclonal anti-human chorionic gonadotropin antibody in women with an ectopic pregnancy," *Fertil Steril* 52:734-8 (1989). These authors used mouse monoclonal antibodies. In a more recent article using human monoclonal antibodies, it was shown that humanized antibodies could be utilized in the treatment of CMV after renal transplantation. Skarp et al., "Use of a human monoclonal anti-cytomegalovirus antibody for the treatment of severe cytomegalovirus after renal transplantation," *Transplant Proc* 22:234 (1990). Finally, the general advantages of human monoclonal antibodies over mouse monoclonal antibodies has been described. Ehrlich et al., "Human and primate monoclonal antibodies for in vivo therapy," *Clin Chem* 34:1681-8 (1988).

In addition to being given systemically, these particular monoclonal antibodies could also be applied directly within the intrauterine cavity and possibly within the fallopian tube.

In another aspect of this invention, a method of sterilizing a mammal is provided. By the method of this invention, a mammal is sterilized by administering to the mammal a TUN antigen in an amount sufficient to raise antibodies to TUN, whereby the probability that a conceptus will become implanted in the uterus in decreased.

Since TUN appears in trophoblasts during pregnancy, a novel method of permanent female sterilization based on TUN immunization is provided. These antibodies would bind to TUN secreted by the mammal e.g., trophoblastic cells. The presence of these antibodies may inhibit fertilization, and prevent implantation of the blastocyst or otherwise induce sterilization. In addition, if a blastocyst were to initiate implantation, the presence of these antibodies are expected to prevent the further attachment of the developing trophoblast to the endometrial stroma, thus ending the gestation.

Mammals could be immunized against TUN by using the whole molecule or just the IIICS domain of TUN. Generally the protein can be dissolved at between about 1 to 50 μg/ml in sterile saline or saline with 0.4 mg aluminum hydroxide per ml as a vehicle. Generally 0.5 to 1.0 ml of the protein solution is injected intramuscularly and then followed by booster injections at one and 6-12 months after the initial immunization. Such immunizations thus prevents antibodies from developing against portions of TUN in common with normal adult plasma or cellular fibronectin.

There is precedence for immunizing patients and animals against various products of pregnancy to induce contraception. For example, 88 subjects which were immunized with a β-hCG base vaccine have been investigated. Kharat et al., "Analysis of menstrual records of women immunized with anti-hCG vaccines inducing antibodies partially cross-reactive with hLH," *Contraception* 41:293-9 (1990). In animals, it has been shown that antibodies made against pig zonae pellucidae could induce contraception in mares. Liu et al., "Contraception in mares heteroimmunized with pig zonae pellucidae," *J Reprod Fertil* 85:19-29 (1989). Finally, in a study in dogs, it has been shown that contraception could be induced by immunizing dogs against gonadotropin releasing hormone. Gonzalez et al., "Immunological approaches to contraception in dogs," *J Reprod Fertil Suppl* 39:189-98 (1989).

EXAMPLES

Example 1

Localization of TUN Within Human Pregnancy Tissues

5 μm sections from Bouin's-fixed and paraffin-embedded tissue were placed on glass slides previously coated with a film of 1% poly-d-lysine, 30-70,000 daltons molecular weight (Sigma), dried at temperatures no greater than 60° C. and stored at room temperature until used. Immunoperoxidase staining was carried out as described previously. Kliman et al., "Purification, characterization and in vitro differentiation of cytotrophoblasts from human term placentae," *Endocrinol.* 118: 1567-1582 (1986). FDC-6, a product of hybridoma cell line ATCC HB9018 (American Type Culture Collection, Rockville, Md.), was utilized at a concentration of 4 μg/ml. Control slides were incubated with undiluted ATCC P3X63Ag8 mouse myeloma cell line supernatant. The results are depicted in FIG. 1 a)-d) and are summarized below:

a) Utero-placental junction from a 16-week gestation exhibited a distinct band of TUN staining (arrow heads) at the zone of contact between extravillous trophoblasts and decidualized endometrium (D). Note the positively staining cell column (C) emanating from the negatively stained chorionic villi (V).

b) Higher power of the same utero-placental junction reveals that TUN staining is largely extracellular around the extravillous trophoblasts (T), Decidua (D), and villous (V).

c) A distinct band of TUN staining is seen at the junction of the extravillous trophoblasts (T) and fallopian tube (FT) in a tubal pregnancy. The extravillous trophoblasts nearest the junction have a heavy ECM deposit of TUN, while the trophoblasts farther away from the trophotubal junction appear to have a delicate membrane stained pattern (arrow heads). Note the negatively stained cytotrophoblasts and syncytiotrophoblasts of the chorionic villi (V).

d) High power view from the edge of the trophoblastic shell of a 20 day post-conception gestation. Note the intracytoplasmic, perinuclear TUN staining (arrows) and the delicate intercellular-membrane staining (arrow heads). Bars represent 100 μm (a), 20 μm (b, c), and 5 μm (d).

Conclusions

A universal staining pattern for FDC-6 reactivity was found within human pregnancy tissue. As shown in the histologic section from an intact 16 week human implantation site, specific and intense staining for TUN was consistently noted within the attachment zone of the placental-uterine junction (FIG. 1a). At higher magnification (FIG. 1b), it can be seen that this dark staining is localized to the ECM surrounding the extravillous anchoring trophoblasts and trophoblast cell columns of the placenta. Both placental villi and uterine tissue remote from the implantation site were consistently negative for TUN. This specificity of staining in multiple different placental attachment sites was observed across gestational ages ranging from 20 days post-conception until term. Furthermore, TUN was present around the anchoring trophoblast ECM of extrauterine pregnancies, including implantations within the fallopian tube (FIG. 1c), ovary, and cervix. These results clearly link TUN deposition in the ECM with the implanting trophoblasts, whether intra- or extrauterine in location. In one unusual specimen from a uterine curettage collected during a cycle of conception (fertilization day 20) (FIG. 1d), cytotrophoblasts at the edge of the trophoblastic shell contained intracytoplasmic and membrane associated TUN, indicating very early trophoblast production of this implantation site protein. TUN was also prominent within the ECM of the chorionic membrane at the chorionic-decidual junction. This follows the same pattern as described above, since the chorion is actually the remnant of the trophoblastic shell which did not form a placenta and only contains extravillous trophoblasts attached to maternal decidual stroma. The specificity of staining with FDC-6 implicates TUN and the IIICS region of the glycoprotein as a trophoblast product involved in implantation and placental attachment, unlike polyclonal antibodies previously studied. Earl et al., "Fibronectin and Laminin in the Early Human Placenta," Placenta 11, 223–231 (1990).

Example 2

Human Trophoblasts in Culture Synthesize TUN de novo

Human cytotrophoblasts were purified as previously described. Kliman et al., "Purification, characterization and in vitro differentiation of cytotrophoblasts from human term placentae," *Endocrinol.* 118: 1567–1582 (1986). The cytotrophoblasts were cultured in Dulbecco's Modified Eagles' Medium (DMEM) containing 25 mM glucose and 25 mM HEPES (DMEM-HG) supplemented with gentamicin (50 µg/ml), glutamine (4 mM), and 20% (v/v) heat-inactivated fetal calf serum. For preparation of cell extracts, cells were washed with phosphate buffered saline, scraped from the culture dish, and total cellular protein was extracted with an SDS-didechoate buffer. One hundred µg of total trophoblast cellular protein and 100 µl of unconcentrated conditioned media was electrophoresed on a 6% SDS-PAGE gel under reducing conditions. The gels were electrotransferred to nitrocellulose (Schleicher and Schull) overnight, incubated with FDC-6 as primary antibody (8 µg/ml), with immunodetection using a biotinylated anti-mouse secondary antibody (ABC "Vectastain", Vector Labs, Burlingame, Calif.). This immunoblot method detected as little as 50 ng of intact TUN subunit, with a molecular weight of approximately 250 kD. As depicted in FIG. 2 (a) and (b):

a) Trophoblast cell extract contains barely detectable TUN at time zero (lane a), with some synthesis initiated after 24 h in culture (lane b). Significantly more TUN was present in the cell extracts after 48, 72 and 96 h (lanes d, f, g) whereas 1.5 mM cAMP significantly inhibited trophoblast TUN synthesis (lanes c, e).

b) Trophoblast conditioned media mirrored the cell extract for TUN content. No TUN was detected in control media containing 20% fetal calf serum (lane h), but a faint TUN signal was present in media from 24 h cells (lane i). Significant TUN secretion was noted at 36, 48, 72, and 96 h (lanes k, l, n, o), but not in the presence of 1.5 mM 8-bromo-cAMP (lane M).

Conclusions

As depicted in FIG. 2, cell protein extract from freshly purified villous cytotrophoblasts contained barely detectable TUN on ELISA (<50 ng/mg cell protein), in agreement with the negative villous staining for TUN in the placenta. A small quantity of TUN was present intracellularly after 24 h, (125 ng/mg cell protein), suggesting that TUN synthesis had been initiated by the cultured cells. After 96 h, trophoblasts contained 18 fold more TUN (2200 ng/mg cell protein) than the 24 hour cells, representing 0.2% of total trophoblast cell protein. Thus cytotrophoblasts, while not synthesizing TUN in vivo, are induced in culture to produce significant TUN. It was also determined that cultured trophoblasts secrete TUN. Although very little TUN could be measured in conditioned media from the first 24 h of culture, during the time interval from 24 to 48 h the media concentration of TUN averaged 4.5 µg/ml. This result indicated trophoblast secretion of newly synthesized TUN into the culture media. Based on ELISA, 100 percent of trophoblast fibronectin TUN contains the oncofetal domain, and is therefore reactive with FDC-6. Immunoblot analysis with both trophoblast cell extract and media corroborated the ELISA findings, and indicated de novo synthesis and secretion of intact TUN.

Example 3

Cyclic AMp Agonists Inhibit Trophoblast TUN Production

Some cAMP agonists are major inducers of trophoblast hCG synthesis and secretion. Feinman et al., "8-Bromo-3'5' AMP stimulates the endocrine activity of human cytotrophoblasts in culture," *J. Clin End Metab* 63:1211–1217 (1986).

Trophoblasts, cultured as described in Example 2, were treated with various concentrations of 8-bromo-cAMP. At standard concentrations of 1.0 to 1.5 mM 8-bromo-cAMP, no TUN was detected by a sensitive ELISA. Treatment of freshly isolated cytotrophoblasts for only 6 h with 1.5 mM 8-bromo-cAMP also prevented de novo synthesis and secretion. A concentration as low as 0.05 mM, 8-bromo-cAMP did not completely prevent TUN production, but did result in a 20-fold inhibition of TUN after 48 h, and 30-fold reduction after 72h. Another cAMP agonist, Forskolin, (100 µM) also inhibited TUN production by trophoblasts, but no significant effect was noted with 8-bromo-cGMP or the phorbol ester PMA. Immunocytochemical staining of fixed cultured trophoblasts after 48 hours demonstrated TUN within the cytoplasm and on the cell surface in 100% of the cells. Cells treated with 1.5 mM 8-bromo-cAMP contained no TUN immunostaining, consistent with the immunoblot results. These results demonstrate the important role for cAMP agonists in regulating TUN synthesis.

Example 4

Trophoblast-ECM Interactions in vitro: Synthesis and Localization of TUN

Ice cold MATRIGEL was applied to a sterile petri dish, the dish was tilted to spread the solution out, and then placed into a humid 37° C. incubator for 1 hour to promote gelling The ECM gel was then minced into 3-5 mm cubes with a sterile scalpel and individual pieces were placed into 1 ml of a $1 \times 10^6$ cells/ml suspension of human cytotrophoblasts prepared as described in Example 2. The cell suspensions were cultured in loosely capped sterile $17 \times 100$ mm polypropylene snap-top tubes at 37° C. in an atmosphere of humidified 95% air—5% $CO_2$ while being gyrated on an angled (~30°) rotator (Red Rotor, Hoefer Scientific Instruments, San Francisco, Calif.) at a setting of five. Media was changed every 24 hours by centrifugation of the tubes at low speed at room temperature, aspiration of the spent media, followed by replacement with fresh media. After 48 of suspension culture, the MATRIGEL fragments were fixed in Bouin's solution and processed as described in Example 1. As seen in FIG. 3:

a) Cross-section of a tongue of trophoblasts (T) which have penetrated into the MATRIGEL (M) fragment. The majority of the TUN immunoreactivity is restricted to the periphery of the trophoblastic aggregate, at the junction with the surrounding MATRIGEL.

b) High power view of the edge of the aggregate at the trophoblas MATRIGEL (M) junction. Note that the trophoblasts (T) have synthesized and secreted TUN into the ECM adjacent to the MATRIGEL (arrow heads). Bars represent 20μm (a) and 5 μm (b).

Conclusions

Figure 1D:
Figure 1A:
Figure 1C:
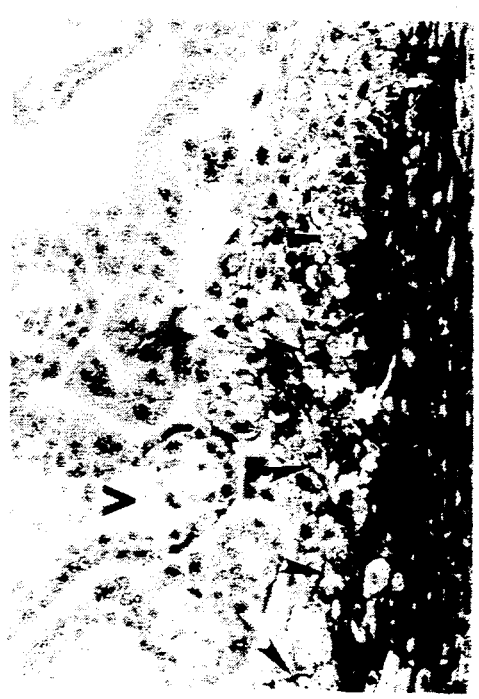

The immunohistochemical analysis of fixed sections with FDC-6 revealed a specific band of TUN at the trophoblast-ECM interface (FIG. 3a), reminiscent of the staining pattern seen at the edge of the early trophoblastic shell specimen (FIG. 1d). Prominent TUN was seen primarily within the extracellular space and MATRIGEL at sites of trophoblast contact (FIG. 3b). Cytotrophoblast differentiation in vitro has been previously characterized morphologically by syncytial formation, and biochemically by the production of placental hormones. Feinman et al., "8-Bromo-3'5' AMP stimulates the endocrine activity of human cytotrophoblasts in culture," *J. Clin End Metab* 63: 1211-1217 (1986) and Kliman et al., *Endocrinology*, 118:1567-1582 (1986).

This example demonstrates that TUN is another important marker which defines a differentiated form of trophoblast capable of penetrating and anchoring to the ECM.

Example 5

Localization and Identification of TUN in Non-Human Primate Pregnancy Tissues and Fluid High concentrations of TUN have been identified in amniotic fluid obtained from a gestational day 110 long-tailed macaque monkey pregnancy. In order to determine the cellular localization of TUN in non-human primates, pregnancy tissues from rhesus monkeys were obtained from early, mid, and late gestations. As in humans, a specific zone of extracellular matrix staining was identified in the placental-uterine interface, where anchoring trophoblasts make contact and attach to the uterine decidua. In post-fertilization days 18 to 25 monkey implantation sites, both intracellular and ECM staining were noted around the implanting trophoblasts, demonstrating that active synthesis of TUN occurs during non-human primate implantation. Manipulation of monkey TUN should be useful for therapeutic and diagnostic applications in monkeys and other mammals for fertility enhancement, contraception, contragestion, and methods of diagnosis.

What is claimed is:

1. A method of increasing the success rate of assisted implantation comprising the steps of:
   contacting a mammalian ovum or conceptus with an amount of tropho-uteronectin sufficient to increase the implantation rate of said conceptus or of a conceptus derived from said ovum and; introducing said ovum or conceptus into the reproductive tract of a female mammal.

2. The method of claim 1 wherein the mammal is a human.

* * * * *

UNITED STATES PATENT AND TRADEMARK OFFICE
CERTIFICATE OF CORRECTION

PATENT NO. : 5,276,017
DATED : JANUARY 4, 1994
INVENTOR(S) : FEINBERG ET AL.

It is certified that error appears in the above-indentified patent and that said Letters Patent is hereby corrected as shown below:

On title page, item [56] under Other Publication, Page 2, line 8, please delete "end Metab" and insert therefor --End Metab--.

Column 7, line 10, please delete "IgGI" and insert therefor --IgG1--.

Column 13, line 50, please delete "*Ther* 90:288-92" and insert therefor --*Ther* 290:288-92--.

Column 13, line 58, please delete "oligodeoxynuoleotide" and insert therefor --oligodeoxynucleotide--.

Column 18, line 48, please delete "Cyclic AMp" and insert therefor --Cyclic AMP--.

Column 19, line 15 please insert --.-- between "gelling The ECM".

Column 19, line 38, please delete "trophoblas-MATRIGEL" and insert therefor --trophoblast-MATRIGEL--.

Signed and Sealed this

Fourth Day of April, 1995

Attest:

BRUCE LEHMAN

*Attesting Officer*     *Commissioner of Patents and Trademarks*